(12) United States Patent
Yanagisawa et al.

(10) Patent No.: US 8,907,085 B2
(45) Date of Patent: Dec. 9, 2014

(54) HYDRATE OF SULFONYLUREA COMPOUND, PROCESS FOR PRODUCING THE SAME AND SUSPENSION FORMULATION CONTAINING THE SAME

(75) Inventors: Yu Yanagisawa, Osaka (JP); Daisaku Kamo, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/334,278

(22) Filed: Dec. 22, 2011

(65) Prior Publication Data

US 2012/0165196 A1 Jun. 28, 2012

(30) Foreign Application Priority Data

Dec. 27, 2010 (JP) ................................. 2010-289619

(51) Int. Cl.
*C07D 487/04* (2006.01)
(52) U.S. Cl.
USPC ....................................................... 544/236
(58) Field of Classification Search
USPC ..................................... 544/236; 514/252.05
See application file for complete search history.

(56) References Cited

U.S. PATENT DOCUMENTS

| 5,017,212 A | 5/1991 | Ishida et al. |
| 2005/0032650 A1 | 2/2005 | Tanaka et al. |

FOREIGN PATENT DOCUMENTS

| CN | 87102123 A | 10/1987 | | |
| CN | 1617666 A | 5/2005 | | |
| EP | 1466527 | * 10/2004 | ........... | C07D 471/04 |
| EP | 1466527 A1 | 10/2004 | | |
| EP | 1891856 A1 | 2/2008 | | |
| JP | 2006-257082 A | 9/2006 | | |
| JP | 2009-209101 A | 9/2009 | | |
| WO | 03/061388 A1 | 7/2003 | | |

OTHER PUBLICATIONS

Spanish Search Report, dated Nov. 21, 2012, issued in corresponding Spanish Patent Application No. 201132104.
Brittain, "Polymorphism in Pharmaceutical Solids," Second Edition, vol. 192, Informa Healthcare, 2009 (10 pages).
The Office Action No. 3063 (including partial English translation), dated Mar. 7, 2014, issued in the corresponding Colombian Patent Application No. 11178631.
The Office Action (including English translation), dated Nov. 28, 2013, issued in the corresponding Israeli Patent Application No. 216,784.
Drewe et al., "Practical Problems in Accelerated Testing of Pesticide Formulations," Pestic. Sci., vol. 1, Nov.-Dec. 1970, pp. 279-286.
Fujimoto et al., "Preparation of Binapacryl Suspension Concentrates and Their Physical Stability," Pesticide Science Society of Japan, vol. 7, No. 4, Nov. 1982, pp. 499-506.
The Office Action No. 7946 (including an English translation), dated Jul. 8, 2014, issued in the corresponding Colombian Patent Application No. 14122897.
The Resolution No. 42995 (including an English translation), dated Jul. 14, 2014, issued in the corresponding Colombian Patent Application No. 11178631.
English translation of Fujimoto et al., "Preparation of Binapacryl Suspension Concentrates and Their Physical Stability," Journal of Pesticide Science, vol. 7, No. 4, Nov. 1982, pp. 499-506.
The First Office Action (including an English translation), dated Sep. 19, 2014, issued in the corresponding Chinese Patent Application No. 201110437774.7.

* cited by examiner

*Primary Examiner* — Paul V. Ward
(74) *Attorney, Agent, or Firm* — Birch Stewart Kolasch & Birch, LLP

(57) ABSTRACT

The present invention relates to a hydrate of sulfonylurea compound represented by formula (I):

having herbicidal activity, a process for producing the same, a suspension formulation containing the same, and the like.

4 Claims, No Drawings

HYDRATE OF SULFONYLUREA COMPOUND, PROCESS FOR PRODUCING THE SAME AND SUSPENSION FORMULATION CONTAINING THE SAME

FIELD OF THE INVENTION

The present application is filed claiming the priority of the Japanese Patent Application No. 2010-289619 (filed on Dec. 27, 2010), the entire contents of which are herein incorporated by the reference.

The present invention relates to a hydrate of sulfonylurea compound having herbicidal activity, a process for producing the same, a suspension formulation containing the same, and the like.

BACKGROUND OF THE INVENTION

Recently, there is a need for a formulation that allows a herbicidal compound to be sprayed in a more simple way in order to control weeds because of the aging or decreasing population of farmers, and the like. Regarding a solid and poorly water-soluble herbicidal compound, for example, suspension formulations containing said compound, which can be sprayed directly from levee into paddy field under flood irrigation, have been developed for practical use.

EP 1466527 A1 discloses a sulfonylurea compound represented by formula (I):

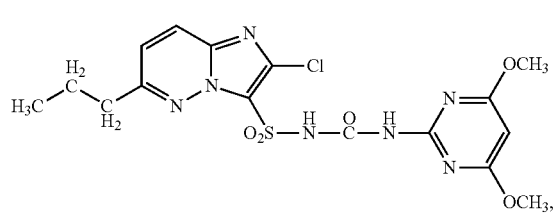

which has herbicidal activity, and a suspension formulation containing said compound.

SUMMARY OF THE INVENTION

In suspension formulations containing a herbicidal compound, the herbicidal compound is generally suspended in water. Such suspension formulations can be produced by, generally, mixing a finely-ground, solid and poorly water-soluble herbicidal compound, a thickening agent, a surfactant and water, and, if necessary, an agricultural formulation additive.

In view of formulation stability such as suspension stability, herbicidal activity, spraying operability, and the like, it is advantageous that solid particles comprising a herbicidal compound in a suspension formulation have a small particle size (about 10 μm or less) immediately after the production of the suspension formulation as well as when using the suspension formulation after storage.

In suspension formulations containing a sulfonylurea compound represented by formula (I), solid particles comprising the sulfonylurea compound generally tend to grow (i.e., the particle size thereof tends to increase) in the suspension formulations over time during the storage period. If suspension formulations after storage are applied, there are sometimes problems that (i) the nozzle of sprayer used is clogged up by the solid particles, (ii) the herbicidal activity is not sufficiently obtained, and (iii) a large amount of precipitate is formed after long storage.

In these circumstances, the present inventors have conducted intensive studies and finally found a novel form of the sulfonylurea compound, which can make solid particles comprising the sulfonylurea compound difficult to grow in the suspension formulation, thereby reaching the present invention.

Namely, the present invention provides the followings:
1. A hydrate (hereinafter sometimes referred to as "the present inventive hydrate") of a sulfonylurea compound represented by formula (I) (hereinafter sometimes referred to as "the present compound"):

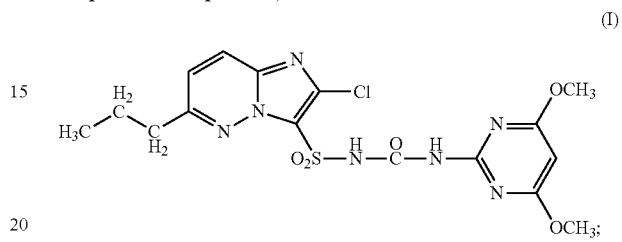

2. The hydrate according to the above item 1, wherein the hydrate is a hemihydrate (hereinafter sometimes referred to as "the present inventive hemihydrate");
3. A suspension formulation (hereinafter sometimes referred to as "the present inventive suspension formulation") obtainable by mixing the hydrate according to the above item 1 or 2, a thickening agent, a surfactant and water;
4. A suspension formulation obtainable by mixing the hydrate according to the above item 1 or 2, a thickening agent, a surfactant, an agricultural formulation additive and water.

EFFECT OF THE INVENTION

According to the present invention, a novel form of the sulfonylurea compound represented by formula (I) (i.e., the present compound), which can make solid particles comprising the present compound difficult to grow in a suspension formulation containing the present compound, and a suspension formulation having superior stability such that the growth of solid particles comprising the present compound (i.e., the increasing of the particle size) is hardly occurred in the suspension formulation over time during the storage period, can be provided.

DETAILED DESCRIPTION OF THE EMBODIMENTS

The present inventive hydrate refers to a hydrate of a sulfonylurea compound represented by formula (I) (i.e., the present compound):

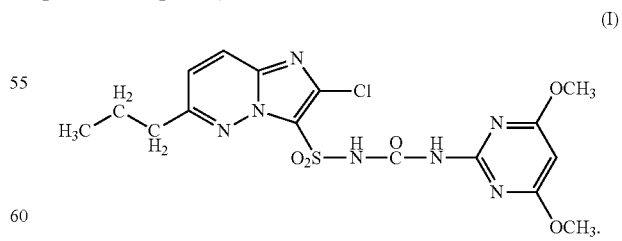

Preferred examples of the hydrate include a hemihydrate (i.e., ½ hydrate).

The present inventive hydrate may be in a mixture with a nonhydrate of the sulfonylurea compound represented by formula (I) (i.e., the present compound). Preferred examples of the mixture include those containing the present inventive hydrate (preferably, consisting essentially only of the present inventive hemihydrate) in an amount of not less than 0.2% by weight based on the total amount of the mixture, and more preferred are those containing the present inventive hydrate (preferably, consisting essentially only of the present inventive hemihydrate) in an amount of not less than 0.8% by weight based on the total amount of the mixture. The upper limit of the proportion of the present inventive hydrate is not particularly limited, but may be not more than 100% by weight based on the total amount of the mixture.

In addition, the present inventive hydrate present in a mixture with a nonhydrate of the present compound includes crystals comprising a nonhydrate of the present compound and the present inventive hydrate (preferably, the present inventive hemihydrate).

The present inventive hydrate can be produced by mixing a nonhydrate of sulfonylurea compound represented by formula (I) (i.e., the present compound) and water, and then stirring the resultant mixture (hereinafter sometimes referred to as "the present inventive production process No. 1").

In addition, the present inventive hydrate can be produced by dissolving a nonhydrate of sulfonylurea compound represented by formula (I) (i.e., the present compound) into a water-containing organic solvent, and then recrystallizing the mixture to obtain crystals (hereinafter sometimes referred to as "the present inventive production process No. 2").

In the present inventive production process No. 1, the present inventive hydrate can be obtained, for example, by (a) mixing a nonhydrate of the present compound with water, and then stirring the resultant mixture, and (b) subjecting the mixture to recrystallization, and then collecting the precipitated crystals by filtration and drying the collected residue under reduced pressure.

The temperature in the stirring of the "mixture of a nonhydrate of the present compound and water" (stirring temperature) in the present inventive production process No. 1 is, for example, from 5° C. to 95° C., preferably from 20° C. to 60° C.

The time in the stirring of the "mixture of a nonhydrate of the present compound and water" (stirring time) in the present inventive production process No. 1 is, for example, 7 days or more. Such process is suitable, for example, when producing the present inventive hydrate (preferably, the present inventive hemihydrate) in a mixture with a nonhydrate of the present compound.

In addition, a production process wherein the stirring time is set for not less than 14 days is suitable, for example, when producing the present inventive hydrate consisting essentially only of the present inventive hemihydrate, but not a mixture with a nonhydrate of the present compound.

The amount of "water" to be used in the present inventive production process No. 1 is preferably an amount not causing any trouble in the stirring of the mixture, and is, for example, from 10 mL to 100 mL, more preferably from 10 mL to 60 mL, relative to 1 g of a nonhydrate of the present compound.

In the present inventive production process No. 1, the present inventive hydrate can be produced in a shorter time by adding the present inventive hydrate produced separately as a seed crystal to a mixture of a nonhydrate of the present compound with water, and then stirring the mixture. The amount of the "hydrate of the present invention produced separately" to be added as a seed crystal is preferably not less than 8 parts by weight relative to 92 parts by weight of a nonhydrate of the present compound.

In the present inventive production process No. 2, the present inventive hydrate can be obtained, for example, by (a) mixing a nonhydrate of the present compound with a water-containing organic solvent, and then stirring the resultant mixture to dissolve the nonhydrate into the organic solvent, (b) ice-cooling the resultant solution, and (c) subjecting the solution to recrystallization, and then collecting the precipitated crystals by filtration and drying the collected crystals under reduced pressure.

Preferably, the production process No. 2 may comprise (a) mixing a nonhydrate of the present compound with a water-containing organic solvent, and then stirring the resultant mixture with warming to dissolve the nonhydrate into the organic solvent and allowing the resultant solution to cool at room temperature, (b) ice-cooling the cooled solution, and (c) subjecting the solution to recrystallization, and then collecting the precipitated crystals by filtration and drying the collected crystals under reduced pressure.

In the step (a), after mixing a nonhydrate of the present compound with a water-containing organic solvent, the temperature of "stirring the resultant mixture to dissolve the nonhydrate into the organic solvent" (stirring temperature) is, for example, from 60° C. to 80° C.

In the step (a), after mixing a nonhydrate of the present compound with a water-containing organic solvent, the time of "stirring the resultant mixture to dissolve the nonhydrate into the organic solvent" (stirring time) is, for example, from 1 to 2 hours.

The "organic solvent" to be used in the present inventive production process No. 2 includes, for example, hydrophilic organic solvents, and the like. Preferred examples thereof include tetrahydrofuran (THF), acetonitrile, methanol, ethanol, dimethylsulfoxide, t-butanol, isopropyl alcohol, and the like, and more preferred examples include tetrahydrofuran (THF), acetonitrile, and the like.

The "water-containing organic solvent" to be used in the present inventive production process No. 2 includes, for example, those having a water content of not less than 1 part by weight relative to 99 parts by weight of the organic solvent. Specific examples thereof include water-containing tetrahydrofuran having a water content of about 1% by weight, water-containing acetonitrile having a water content of about 15% by weight, and the like.

The amount of "water-containing organic solvent" to be used in the present inventive production process No. 2 may be, for example, an amount capable of dissolving the present compound and precipitating the crystals by recrystallization. Specifically, when tetrahydrofuran or acetonitrile is used as the organic solvent, the amount is, for example, from 10 mL to 25 mL relative to 1 g of a nonhydrate of the present compound.

In the present inventive production process No. 2, the present inventive hydrate can be produced in a shorter time by adding the present inventive hydrate produced separately as a seed crystal to a mixture of a nonhydrate of the present compound with a water-containing organic solvent, stirring the mixture to dissolve the nonhydrate into the organic solvent, allowing the solution to cool at room temperature, and then ice-cooling the cooled solution. The preferred amount of the "hydrate of the present invention produced separately" to be added as a seed crystal is, for example, not less than 8 parts by weight relative to 92 parts by weight of a nonhydrate of the present compound.

In the production of the present inventive hydrate, the conversion from a nonhydrate of the present compound to the present inventive hydrate (including the present inventive hydrate present in a mixture with a nonhydrate of the present compound) may be monitored by various analytical methods such as infrared absorption spectrum analysis, water content measurement, thermal analysis, X-ray powder diffraction analysis, and the like.

Specifically, for example, when the "increase in size of the peak corresponding to water molecule" or "shift in the peak" in a test sample is observed by infrared absorption spectrum analysis or the "increase in water content" in a test sample is observed by water content analysis, with reference to a nonhydrate of the present compound as a control sample, it is judged that a nonhydrate of the present compound has been converted to the present inventive hydrate (including the present inventive hydrate present in a mixture with a nonhydrate of the present compound).

As to thermal analysis, when an endotherm peak is detected in the vicinity of 136° C. and the decrease in weight is measured, for example, by thermogravimetric analysis (TG)/differential thermal analysis (DTA), it is judged that a nonhydrate of the present compound has been converted to the present inventive hydrate (including the present inventive hydrate present in a mixture with a nonhydrate of the present compound).

When a peak such as 2θ=9.6°, 11.0° is detected by X-ray powder diffraction (Cu-Kα) analysis, it is judged that a nonhydrate of the present compound has been converted to the present inventive hydrate (including the present inventive hydrate present in a mixture with a nonhydrate of the present compound).

The anhydrate of the sulfonylurea compound represented by formula (I) to be used for producing the present inventive hydrate is produced, for example, by a method as described in paragraphs [0173] and [0174] of EP 1466527 A1 (compound No. 36).

Hereinafter, the present inventive suspension formulation will be explained.

The present inventive suspension formulation can be obtained by mixing the present inventive hydrate, a thickening agent, a surfactant and water, and, if necessary, an agricultural formulation additive. Namely, the present inventive suspension formulation is a herbicidal composition obtained by dispersing or dissolving the present inventive hydrate, a thickening agent and a surfactant, and, if necessary, an agricultural formulation additive into water.

In the suspension formulation, solid particles comprising the present compound are dispersed in water in the form of fine particles. The average particle size of the fine particles is, for example, not more than 10 μm, preferably 0.2 μm to 5 μm.

When the present inventive hydrate is present in a mixture with a nonhydrate of the present compound, the amount of the present inventive hydrate in the mixture is, for example, not less than 0.2% by weight and less than 100% by weight relative to the amount of the nonhydrate of the present compound. Namely, the proportion (weight ratio) of a nonhydrate of the present compound to the present inventive hydrate is, for example, from 99.8:0.2 to 0:100, preferably from 99.2:0.8 to 0:100.

The content of the present inventive hydrate (including the present inventive hydrate present in a mixture with a nonhydrate of the present compound) in the present inventive suspension formulation is, for example, from 0.5% by weight to 50% by weight, preferably from 1% by weight to 40% by weight.

The content of thickening agent in the present inventive suspension formulation is, for example, from 0.01% by weight to 5% by weight, preferably from 0.1% by weight to 3% by weight.

The content of surfactant in the present inventive suspension formulation is, for example, from 0.1% by weight to 10% by weight.

The water content in the present inventive suspension formulation is, for example, from 30% by weight to 90% by weight, preferably from 50% by weight to 80% by weight.

The present inventive suspension formulation may contain other pesticidal compounds, in addition to a pesticidal compound included in the present inventive hydrate (including the present inventive hydrate present in a mixture with a nonhydrate of the present compound). Examples of the "other pesticidal compound" include simetryn, dymron, propanil, mefenaset, phentolazamide, ethobenzanide, swep, oxadiclomefone, oxadiazolone, pyrazolate, prodiamine, cafenstrole, pentoxazone, clomeprop, pyriphthalide, benzobicyclon, bromobutide, pyraclonil, imazosulfuron, sulfosulfuron, and the like.

When the "other pesticidal compound" is contained in the present inventive suspension formulation, the amount of all the pesticidal compounds in the present inventive suspension formulation [i.e., the total amount of a pesticidal compound included in the present inventive hydrate (including the present inventive hydrate present in a mixture with a nonhydrate of the present compound) and the "other pesticidal compound"] is, for example, 0.5% by weight to 50% by weight, preferably 1% by weight to 40% by weight.

Examples of the thickening agent to be used in the present inventive suspension formulation include xanthan gum, guar gum, gum arabic, casein, dextrin, carboxymethyl cellulose or a salt thereof (for example, sodium salt, calcium salt, etc.), sodium carboxymethylstarch, sodium alginate, hydroxyethyl cellulose, carboxyethyl cellulose, methyl cellulose, hydroxypropyl cellulose, hydroxyethyl cellulose, polyvinyl alcohol, polyacrylic acid or a derivative thereof, montmorillonite, talc, saponite, and the like.

In the present invention, carboxymethyl cellulose is generally used in the form of a salt. The preferred carboxymethyl cellulose salt to be used in the present inventive suspension formulation includes, for example, those having a relatively low viscosity when being dissolved in water, specifically a viscosity of from 10 mPa·s to 100 mPa·s (type B viscometer, 60 rpm, 25° C.) in 2% by weight aqueous solution.

Typical examples of carboxymethyl cellulose salt include those commercially available, such as CELLOGEN 6A (manufactured by Dai-ichi Kogyo Seiyaku Co., Ltd.), CELLOGEN 7A (manufactured by Dai-ichi Kogyo Seiyaku Co., Ltd.), CMC DAICEL 1110 (manufactured by Daicel Chemical Industry, Ltd.) and CMC DAICEL 1210 (manufactured by Daicel Chemical Industry, Ltd.).

Examples of the surfactant to be used in the present inventive suspension formulation include anionic surfactants such as polyoxyethylene arylphenyl ether phosphoric acid salts (e.g., NEWKALGEN FS-3EG, NEWKALGEN FS-3PG, manufactured by Takemoto Oil & Fat Co., Ltd.), alkylsulfuric acid salts (e.g., MONOGEN Y-500, manufactured by Dai-ichi Kogyo Seiyaku Co., Ltd.), polyoxyethylene arylphenyl ether sulfuric acid salts (e.g., AGRISOL FL-2017, manufactured by Kao Corporation), polyoxyalkylene arylphenyl ether sulfuric acid salts (e.g., NEWKALGEN FS-7, manufactured by Takemoto Oil & Fat Co., Ltd.), dioctylsulfosuccinic acid salts (e.g., NEOCOL YSK: manufactured by Dai-ichi Kogyo Seiyaku Co., Ltd., SANMORIN OT70: manufactured by Sanyo Chemical Industries, Ltd.), and the like; and nonionic surfactants such as sucrose fatty acid esters (e.g., NEWKALGEN FS-100, manufactured by Takemoto Oil & Fat Co., Ltd.), polyoxyethylene polyoxypropylene block polymers (e.g., NEWPOL PE68: manufactured by Sanyo Chemical Industries, Ltd.), polyoxyalkylene polyalkylene polyamine (e.g., NEWKALGEN D-3020, manufactured by Takemoto Oil & Fat Co., Ltd.), polyoxyethylene alkylphenyl ether (e.g., NEWKALGEN D-410, manufactured by Takemoto Oil & Fat Co., Ltd.), polyoxyethylene aryl phenyl ether formaldehyde condensates (e.g., NEWKALGEN E-300, manufactured by Takemoto Oil & Fat Co., Ltd.), and the like.

The present inventive suspension formulation may contain two or more surfactants as mentioned above. In this case, it is preferable to use a combination of at least one anionic surfactant and at least one nonionic surfactant.

The water to be used in the present inventive suspension formulation may be those used for conventional herbicidal composition, for example, tap water, well water, ion-exchanged water, and the like.

The agricultural formulation additive to be used in the present inventive suspension formulation includes anti-freezing agents, pH adjusters, antifoaming agents, preservatives, and the like.

Examples of the "anti-freezing agent" include ethylene glycol, diethylene glycol, glycerin, propylene glycol, and the like.

Examples of the "pH adjuster" include citric acid monohydrate, sorbic acid, potassium sorbate, and the like.

Examples of the "antifoaming agent" include silicone-based antifoaming agents, and the like.

Examples of the "preservative" include butylparaben (n-butyl para-hydroxybenzoate), sorbic acid, potassium sorbate, and the like.

The content of the agricultural formulation additive in the present inventive suspension formulation may vary depending on the amount of the present inventive hydrate (including the present inventive hydrate present in a mixture with a nonhydrate of the present compound) to be used, the kind of the surfactant, and the like.

The content of the anti-freezing agent in the present inventive suspension formulation is, for example, 1% by weight to 20% by weight, preferably 3% by weight to 12% by weight.

The content of the pH adjuster in the present inventive suspension formulation is, for example, 0.01% by weight to 5% by weight, preferably 0.5% by weight to 3% by weight.

The content of the antifoaming agent in the present inventive suspension formulation is, for example, 0.05% by weight to 0.5% by weight, preferably 0.05% by weight to 0.3% by weight.

The content of the preservative in the present inventive suspension formulation is, for example, 0.01% by weight to 3% by weight, preferably 0.01% by weight to 1.5% by weight.

The present inventive suspension formulation may be formulated, for example, by the following processes.

<Formulation Process No. 1>

A process comprising mixing the present inventive hydrate (including the present inventive hydrate present in a mixture with a nonhydrate of the present compound), thickening agent, a surfactant and water, and optionally the "other pesticidal compound" and, if necessary, an agricultural formulation additive, and then thoroughly stirring and mixing the mixture, for example, by a high speed stirrer, and finely-grinding and dispersing the mixture, for example, by a wet-pulverizer such as dynomill and micro-fluidizer.

<Formulation Process No. 2>

A process comprising finely-grinding the present inventive hydrate (including the present inventive hydrate present in a mixture with a nonhydrate of the present compound) by a dry-pulverizer such as jetmizer, adding the hydrate together with other components to water, and then stirring and mixing the mixture, for example, by a high speed stirrer for about 30 to 90 minutes to disperse the mixture.

The present inventive suspension formulation can be used by spraying itself or, if desired, after dilution with water, according to known methods. For example, the present inventive suspension formulation can be sprayed directly from levee into paddy field under flood irrigation and the like. In this case, a vessel containing the present inventive suspension formulation is shaken slightly before use, and then the formulation is sprayed in portions along levee. When the present inventive suspension formulation is sprayed after dilution with water, the water dilution is sprayed by using known spraying devices on the surface of soil, stem or leaves, or the like in paddy field, dry field, orchard, turf, non-cultivated field, and the like. In addition, the water dilution can be used in a seed treatment, nursery box treatment, and the like.

EXAMPLES

The present invention is further described below in detail with reference to examples. The present invention is not limited to the examples.

For water content analysis, CA-07 type water-content measuring instrument (manufactured by Mitsubishi Chemical Corporation) was used.

For infrared absorption spectrum analysis, Fourier transform infrared spectrophotometer, Varian Fast Image 670-IR (manufactured by Varian Inc.) was used. The measurement conditions were as follows:

Detector: DTGS
Scans: 32
Scan speed: 5 kHz

For thermal analysis, TG/DTA6200R (manufactured by SII NanoTechnology Inc.) was used.

For X-ray powder diffraction (Cu-K$\alpha$) analysis, powder X-ray diffractometer RINT2500V (manufactured by Rigaku Corporation) was used. The measurement conditions were as follows:

Target: Cu-$\alpha$
Voltage: 40 kV
Current: 300 mA

For proton nuclear magnetic resonance spectrum analysis, DPX300 (manufactured by Bruker Corporation) was used. Tetramethylsilane was used as an internal standard substance, and all delta values were represented as ppm.

Production Example 1

To 217.8 g of the sulfonylurea compound represented by formula (I) (i.e., a nonhydrate of the present compound, hereinafter sometimes referred to as "sample A") produced by a method described in paragraphs [0173] and [0174] of EP 1466527 A1) (Compound No. 36) was added 2413 mL of tetrahydrofuran (THF) having a water content of 1.0% by weight. The resultant mixture was stirred at 70° C. for 1 hour to dissolve the sample A (i.e., a nonhydrate of the present compound) into the above THF. The resultant solution was allowed to cool to room temperature, and then the cooled solution was ice-cooled. After ice-cooling, the crystals precipitated by recrystallization were collected by filtration, and the collected crystals were dried under reduced pressure to obtain 121.8 g of dried crystals (i.e., the present inventive hemihydrate, hereinafter sometimes referred to as "sample B").

As test samples, the sample A and the sample B were subjected to proton nuclear magnetic resonance spectrum analysis (referred to as "$^1$H-NMR" in Table 1), infrared absorption spectrum analysis (referred to as "IR" in Table 1), water content measurement (referred to as "water content" in Table 1), X-ray powder diffraction (Cu-Kα) analysis (referred to as "XRD(2θ)" in Table 1), and thermal analysis (referred to as "TG/DTA" in Table 1). As a result, some characteristic values were obtained (see Table 1).

The proton nuclear magnetic resonance spectrum of the sample A was identical with that of the sample B. On the other hand, peak corresponding to water molecule in infrared absorption spectrum and water content measured by water content analysis were different between the sample A and the sample B.

The sample A and the sample B had different characteristics in terms of crystal diffraction pattern by X-ray powder diffraction (Cu-Kα) analysis.

Further, the sample A and the sample B were different in endotherm peaks observed by thermal analysis. Specifically, the sample B had an endotherm peak at 136° C., in addition to an endotherm peak at 208° C. as observed in the sample A. TG was decreased by 1.9%. Said value was identical with the theoretical water content, 1.9%, when the present compound is a hemihydrate. Therefore, it was confirmed that the sample A was in the form of a nonhydrate, and the sample B was in the form of a hemihydrate.

TABLE 1

|  | Sample A | Sample B |
| --- | --- | --- |
| $^1$H-NMR (DMSO-$d_6$, δ) | 0.70 (3H, t, J = 7.3 Hz), 1.4-1.5 (2H, m), 2.6-2.7 (2H, m), 3.97 (6H, s), 6.08 (1H, s), 7.57 (1H, d, J = 9.4 Hz), 8.26 (1H, d, J = 9.4 Hz), 10.68 (1H, brs), 13.4-13.5 (1H, m) | 0.70 (3H, t, J = 7.3 Hz), 1.4-1.5 (2H, m), 2.6-2.7 (2H, m), 3.97 (6H, s), 6.08 (1H, s), 7.57 (1H, d, J = 9.4 Hz), 8.26 (1H, d, J = 9.4 Hz), 10.68 (1H, brs), 13.4-13.5 (1H, m) |
| IR | 3649 cm$^{-1}$ | 3638 cm$^{-1}$ |
| Water content | 0.06% | 1.90% |
| XRD(2θ) | 6.2 8.6 9.1 13.7 15.4 | 9.6 11.0 |
| TG/DTA | 208° C. (endotherm) | 136° C. (endotherm, decrease of TG: 1.9%) 208° C. (endotherm) |

Production Example 2

Firstly, 852 mg of the sample A (i.e., a nonhydrate of the present compound) was mixed with 50 mL of a deionized water, and then the resultant mixture was started to stir by a stirrer at room temperature. Two (2) days, 7 days and 14 days after the start of stirring, each 10-mL portion of the resultant mixture was collected. The collected mixtures were independently subjected to filtration, collected the precipitated crystals obtained by recrystallization, and then dried the collected crystals under reduced pressure to obtain dried crystals. These crystals were classified into three types depending on the stirring time, i.e., 107 mg of dried crystals (hereinafter sometimes referred to as "sample C") for the portion collected after 2 days, 143 mg of dried crystals (hereinafter sometimes referred to as "sample D") for the portion collected after 7 days, and 144 mg of dried crystals (hereinafter sometimes referred to as "sample E") for the portion collected after 14 days.

Each of the thus obtained samples was subjected to X-ray powder diffraction (Cu-Kα) analysis. As a result, it was confirmed that (i) the sample C was a nonhydrate, (ii) the sample D was the present inventive hemihydrate present in a mixture of a nonhydrate (a mixture of a hemihydrate and a nonhydrate, containing 9.1% by weight of the hemihydrate), and (iii) the sample E was the present inventive hemihydrate (the present inventive hydrate consisting essentially only of the present inventive hemihydrate).

Some of the present inventive hemihydrates in a mixture with a nonhydrate, which are different from the sample D as described in the above (ii), are shown in Table 2 along with the "sample symbol" and the "content (% by weight) of hemihydrate in the mixture".

TABLE 2

| Sample symbol | Content (% by weight) of hemihydrate in the mixture |
| --- | --- |
| Sample G | 7.9 |
| Sample H | 5.7 |
| Sample I | 5.6 |
| Sample J | 0.9 |
| Sample K | 0.5 |
| Sample L | 0.3 |
| Sample M | 0.2 |

Production Example 3

A mixture obtained by mixing 1.8 parts by weight of the sample B (i.e., the present inventive hemihydrate) as produced in Production Example 1, 0.1 parts by weight of sorbic acid, 0.3 parts by weight of a silicone-based antifoaming agent (Antifoam E-20, manufactured by Kao Corporation), 0.5 parts by weight of sucrose fatty acid ester (NEWKALGEN FS-100, manufactured by Takemoto Oil & Fat Co., Ltd.), 1.5 parts by weight of polyoxyethylenearyl phenyl ether phosphoric acid salt (NEW KALGEN FS-3PG, manufactured by Takemoto Oil & Fat Co., Ltd.), 0.35 parts by weight of sodium montmorillonite (KUNIPIA F, manufactured by Kuminine Industries Co., Ltd.), and 30.45 parts by weight of ion-exchanged water, and they were mixed and dispersed, then, wet-pulverized using Dynomill KDL (manufactured by Shinmaru Enterprises Corporation) to obtain an aqueous suspension (1) of the sample B.

On the other hand, 1.0 part by weight of sodium carboxymethylcellulose (CELLOGEN 7A, manufactured by Dai-ichi Kogyo Seiyaku Co., Ltd.), 0.65 parts by weight of sodium montmorillonite (KUNIPIA F, manufactured by Kuminine Industries Co., Ltd.), and 0.1 parts by weight of xanthan gum (Rhodopol 23, manufactured by Rhodia Nicca) were added to 56.65 parts by weight of ion-exchanged water, dissolved and dispersed to obtain a solution (1) of thickening agent. Then, 58.4 parts by weight of the thus obtained solution (1) of thickening agent, 35 parts by weight of the aqueous suspension (1) of the sample B as obtained above, and 6.6 parts by weight of propylene glycol were mixed to become 100 parts by weight in total, and then stirred and mixed the resultant mixture to obtain a suspension formulation of the present invention (hereinafter sometimes referred to as "suspension formulation (1)") containing the sample B (i.e., the present inventive hemihydrate) in an amount of 1.8% by weight.

Production Example 4

A suspension formulation of the present invention (hereinafter sometimes referred to as "suspension formulation (2)") was produced in the same manner as Production Example 3, except for using the sample G (the present inventive hemihydrate present in a mixture with a nonhydrate as shown in Table 2) instead of the sample B (i.e., the present inventive hemihydrate).

Production Example 5

A suspension formulation of the present invention (hereinafter sometimes referred to as "suspension formulation (3)") was produced in the same manner as Production Example 3, except for using the sample H (the present inventive hemihydrate present in a mixture with a nonhydrate as shown in Table 2) instead of the sample B (i.e., the present inventive hemihydrate).

Production Example 6

A suspension formulation of the present invention (hereinafter sometimes referred to as "suspension formulation (4)") was produced in the same manner as Production Example 3, except for using the sample I (the present inventive hemihydrate present in a mixture with a nonhydrate as shown in Table 2) instead of the sample B (i.e., the present inventive hemihydrate).

Production Example 7

A suspension formulation of the present invention (hereinafter sometimes referred to as "suspension formulation (5)") was produced in the same manner as Production Example 3, except for using the sample J (the present inventive hemihydrate present in a mixture with a nonhydrate as shown in Table 2) instead of the sample B (i.e., the present inventive hemihydrate).

Production Example 8

A suspension formulation of the present invention (hereinafter sometimes referred to as "suspension formulation (6)") was produced in the same manner as Production Example 3, except for using the sample K (the present inventive hemihydrate present in a mixture with a nonhydrate as shown in Table 2) instead of the sample B (i.e., the present inventive hemihydrate).

Production Example 9

A suspension formulation of the present invention (hereinafter sometimes referred to as "suspension formulation (7)") was produced in the same manner as Production Example 3, except for using the sample L (the present inventive hemihydrate present in a mixture with a nonhydrate as shown in Table 2) instead of the sample B (i.e., the present inventive hemihydrate).

Production Example 10

A suspension formulation of the present invention (hereinafter sometimes referred to as "suspension formulation (8)") was produced in the same manner as Production Example 3, except for using the sample M (the present inventive hemihydrate present in a mixture with a nonhydrate as shown in Table 2) instead of the sample B (i.e., the present inventive hemihydrate).

Comparative Production Example 1

A comparative suspension formulation (hereinafter sometimes referred to as "suspension formulation (9)") was produced in the same manner as Production Example 3, except for using the sample A (i.e., a nonhydrate of the present compound) instead of the sample B (i.e., the present inventive hemihydrate).

Test Example 1

Particle Size Measurement

For the suspension formulations (1) to (9), the particle size (volume median diameter (μm)) of solid particles comprising the present compound in each suspension formulation was measured by using a laser diffraction type particle size distribution measurement apparatus (HEROS & RODOS, manufactured by Japan Laser Corp., measurement conditions: focus length 20 mm, dispersing medium is ion-exchanged water) (i) immediately after the production, and (ii) after storage in a certain condition. The results are shown in Tables 3 and 4.

TABLE 3

| Suspension formulation | (1) | (2) | (3) | (4) | (5) |
|---|---|---|---|---|---|
| Immediately after production | 2.0 | 1.9 | 2.0 | 1.9 | 1.8 |
| 50° C., 1 week | 1.9 | 2.2 | 2.5 | 2.4 | 2.6 |
| 50° C., 2 weeks | 1.9 | 2.2 | 2.5 | 2.4 | 2.6 |
| 60° C., 1 week | 2.0 | 2.2 | 2.5 | 2.5 | 2.7 |
| 60° C., 2 weeks | 2.0 | 2.3 | 2.5 | 2.5 | 2.7 |

TABLE 4

| Suspension formulation | (6) | (7) | (8) | (9) |
|---|---|---|---|---|
| Immediately after production | 2.0 | 1.8 | 1.8 | 2.0 |
| 50° C., 1 week | 2.9 | 2.9 | 2.8 | 2.8 |
| 50° C., 2 weeks | 2.9 | 2.9 | 2.8 | 13.5 |
| 60° C., 1 week | 3.2 | 3.0 | 3.0 | 11.4 |
| 60° C., 2 weeks | 3.2 | 3.0 | 3.0 | 11.3 |

INDUSTRIAL APPLICABILITY

According to the present invention, a novel form of the sulfonylurea compound represented by formula (I) (i.e., the present compound), which can make solid particles comprising the present compound difficult to grow in a suspension formulation containing the present compound, and a suspension formulation having superior stability such that the growth of solid particles comprising the present compound (i.e., the increasing of the particle size) is hardly occurred in the suspension formulation over time during the storage period, can be provided.

What is claimed is:

1. A process for producing a suspension formulation, which comprises mixing a hemihydrate of a sulfonylurea compound represented by formula (I):

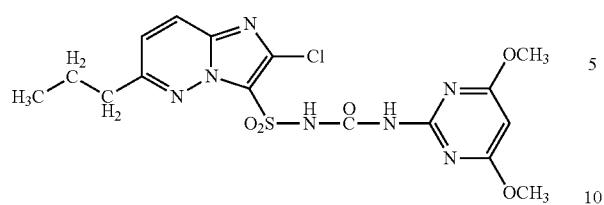

(I)

a thickening agent, a surfactant and water.

2. A suspension formation obtained by mixing the hemihydrate according to claim 1, the thickening agent, the surfactant and water.

3. A suspension formulation obtained by mixing the hemihydrate according to claim 1, the thickening agent, the surfactant, an agricultural formulation additive and water.

4. The process according to claim 1, which comprises mixing the hemihydrate of the sulfonylurea compound represented by formula (I), the thickening agent, the surfactant, an agricultural formulation additive and water.

\* \* \* \* \*